United States Patent [19]

Speranza et al.

[11] Patent Number: 5,239,048

[45] Date of Patent: Aug. 24, 1993

[54] AROMATIC POLYOXYALKYLENE AMIDOAMINES

[75] Inventors: George P. Speranza, Austin; Jiang-Jen Lin, Houston, both of Tex.

[73] Assignee: Texaco Chemical Company, White Plains, N.Y.

[21] Appl. No.: 519,078

[22] Filed: May 4, 1990

Related U.S. Application Data

[63] Continuation-in-part of Ser. No. 78,323, Jul. 27, 1987, abandoned.

[51] Int. Cl.$^5$ .............. C08G 69/26; C08G 69/34; C07C 231/00; C07C 233/00
[52] U.S. Cl. .................. 528/340; 528/343; 528/346; 528/339.3; 564/134; 564/139; 564/144; 564/156
[58] Field of Search ............ 528/340, 343, 346, 339.3; 564/134, 139, 144, 156

[56] References Cited

U.S. PATENT DOCUMENTS

| | | | |
|---|---|---|---|
| Re. 31,522 | 2/1984 | Reider | 528/355 |
| 3,257,342 | 7/1966 | Kwong | 260/18 |
| 3,654,370 | 11/1972 | Yeakey | 260/584 |
| 4,062,819 | 9/1977 | Mains et al. | 260/18 |
| 4,062,820 | 4/1977 | Mitchell et al. | 260/18 |
| 4,119,615 | 12/1978 | Schulze | 528/343 |
| 4,133,803 | 1/1979 | Klein | 528/340 |
| 4,218,351 | 7/1980 | Rasmussen | 260/18 |
| 4,239,635 | 2/1980 | Reider | 252/34 |
| 4,374,741 | 2/1983 | Reider | 528/347 |
| 4,588,783 | 6/1986 | Chang | 525/329.9 |
| 4,595,725 | 10/1986 | Hess et al. | 525/33 |
| 4,751,255 | 4/1988 | Bentley et al. | 521/163 |

Primary Examiner—Herbert J. Lilling
Attorney, Agent, or Firm—Jack H. Park; Kenneth R. Priem; Carl G. Ries

[57] ABSTRACT

Block polyamido polyamine condensation products of an aromatic polycarboxylic acid component with a polyoxyalkylene polyamine component prepared by reacting the polycarboxylic acid component with an amount of the polyoxyalkylene polyamine component sufficient to react each carboxyl group with 1 mole of the polyoxyalkylene polyamine component.

The polyoxyalkylene polyamine being selected from the group consisting of polyoxypropylene diamines, polyoxyethylene diamines, polyoxyethylene/oxypropylene diamines and polyoxypropylene triamines, and the aromatic polycarboxylic acid component being selected from the group consisting of $C_8$ to $C_{28}$ benzene dicarboxylic acids, benzene tricarboxylic acids, naphthalene carboxylates, hemimellitic acid, 1,1,3-trimethyl-3-phenylindan-4',5-dicarboxylic acid, trimellitic acid, and anhydrides and $C_1$ to $C_4$ alkyl esters thereof.

1 Claim, No Drawings

AROMATIC POLYOXYALKYLENE AMIDOAMINES

RELATED APPLICATION

This application is a continuation-in-part of copending Speranza and Lin U.S. Pat. application Ser. No. 07/078,323 filed Jul. 27, 1987 and entitled "Aromatic Amidoamides" now abandoned.

BACKGROUND OF THE INVENTION

1. Technical Field of the Invention

This invention relates to block aromatic polyoxyalkylene amidoamide condensation product. More particularly, this invention relates to novel block aromatic polyoxyalkylene amidoamines condensation products derived from a polyoxyalkylene polyamine component and an aromatic polycarboxylic acid component. Still more particularly, this invention relates to novel block aromatic polyoxyalkylene amidoamide condensation products prepared by reacting an aromatic carboxylic acid component, as hereafter defined, with an amount of a polyoxyalkylene polyamine component, which is suitably a polyoxypropylene diamine or triamine, a polyoxyethylene diamine or a polyoxyethylene/oxypropylene diamine, as hereinafter defined, sufficient to react each carboxyl group of the carboxylic acid component with one mole of the polyoxyalkylene polyamine component to thereby couple, through a condensation reaction, each carboxyl group of the aromatic dicarboxylic acid component to the polyoxyalkylene polyamine component through the formation of an amide linkage. The reaction is preferably conducted at a temperature within the range of about 150° to about 250° C.

The aromatic amidoamine condensation products of the present invention are liquids or amorphous solids, depending upon the starting materials, and can be used as raw materials for a wide variety of purposes such as, for example, as chain extenders for epoxy resins, curing agents for epoxy resins, as raw materials for the manufacture of polyureas, thickening agents, etc. The condensation products may also be used as raw materials for the preparation of fuel and lubricant additives, for textile and fiber treating agents, for the preparation of adhesives, for use in the manufacture of polyureas, for use in encapsulation and molding applications, etc.

2. Prior Art

It is known, as exemplified by Yeakey U.S. Pat. No. 3,654,370 to prepare polyoxyalkylene polyamines by the reductive amination of a polyoxyalkylene polyol. The reductive amination is conducted catalytically in the presence of hydrogen and ammonia and an appropriate reductive amination catalyst, such as a nickel, copper and chromia catalyst. The polyoxyalkylene polyamines that are prepared in this fashion are stable articles of commerce having a wide variety of uses such as those mentioned above. In particular, they have found utility as curing agents for epoxy resins, as plasticizers, as cross linking agents and binders for textiles, and as intermediates in the preparation of polyureas. In general, polyoxyalkylene polyamines having molecular weights ranging from about 200 to about 5,000 can be prepared by the Yeakey process.

Kwang U.S. Pat. No. 3,257,342 is directed to epoxy resins that are cured with a polyamidodiamine prepared by reacting about two molar equivalents of a polyoxyalkylenediamine with an aliphatic dicarboxylic acid.

Klein U.S. Pat. No. 4,133,803 is directed to the preparation of novel thermoplastic adhesive compositions having melting points between 20° and 180° C. prepared by reacting a polyoxypropylene diamine or triamine with an aliphatic or aromatic dicarboxylic acid, ester or anhydride thereof. In his working examples, Klein used approximately equimolar amounts of carboxylic acid and polyamine. However, he states that the molar ratio of the polyoxypropylene diamine or triamine to the dicarboxylic acid may range from about 0.25:1 to about 4.0:1. The thermoplastic adhesives of Klein are made by reacting the polyoxypropylene diamine or triamine with the dicarboxylic acid at about 175° to about 275° C. for about 1 to 12 hours.

The preparation of thermoplastic adhesives is disclosed in Schulze U.S. Pat. No. 4,119,615. The adhesives are prepared by a two-step process. In the first step, about 1 to 4 moles of oxalic acid is reacted with a polyoxyalkylene diamine or triamine, the preferred ratio being a mole ratio of about 1 to 2 moles of oxalic acid per mole of polyoxyalkylene diamine or triamine. This results in the formation of a so-called liquid prepolymer which is then reacted with an alkylene diamine such as ethylene diamine which contain 2 to 18 carbon atoms to provide the resinous polyoxyamide thermoplastic adhesive composition.

Mains et. al. U.S. Pat. No. 4,062,819 is directed to polyamide polyblends wherein one component is a high molecular weight thermoplastic polyamide and the other is a minor amount of a polyamide derived from a high molecular weight dibasic acid. The second component is prepared by reacting a dicarboxylic acid such as "dimer acids" with an aliphatic polyalkylene diamine such as ethylene diamine.

Rieder U.S. Pat. No. 4,239,635 (reissued as Re.30,885) is directed to lubricants modified by the inclusion of diamides. The diamides are carboxylic acid terminated reaction products of an excess of a dicarboxylic acid with a polyoxyalkylene diamine. L Rasmussen U.S. Pat. No. 4,218,351 discloses impact resistant thermoplastic polyamides which are suitable for use as hot melt adhesives and which contain, as a component, a minor amount of an amorphous amide-forming oligomer which is described as a polyoxyalkylene diamine having a number average molecular weight in the range of about 900 to about 5000.

Mitchell, et. al. U.S. Pat. No. 4,062,820 discloses copolyamides derived from a mixture of a polymeric fatty acid and a short chain dibasic acid with a mixture of amines composed of a polyoxyalkylene diamine and a short chain diamine such as ethylenediamine.

Rieder U.S. Pat. No. 4,239,635 is directed to aqueous metal working fluids containing a carboxylic acid group terminated polyoxyalkylene diamine on the alkali metal, ammonium or organic amine salts of the diamides. The diamide is prepared by reacting a dicarboxylic acid with a polyoxyalkylenediamine in a 2:1 mole ratio.

Chang U.S. Pat. No. 4,588,783 relates to heat curable compositions containing polyhydroxyethyl carbonates which are prepared by reacting an amidoamine with an organic carbonate. The block copolymer amidoamines are prepared by reacting a polyester with an equivalent excess of a polyamine, for example, by reacting two moles of isophorone diamine with one mole of dimethylcyclohexane dicarboxylate.

Bently U.S. Pat. No. 4,751,255 is directed to polymeric polyamines prepared by reacting a polycarboxylic acid or an ester thereof with a stoichiometric excess of a polyamine having terminal aminopropoxy groups to provide polymeric polyamines containing 2 to 4 primary amine groups per molecule.

BACKGROUND OF THE PRESENT INVENTION

The polyoxyalkylene polyamines of the type disclosed in Yeakey U.S. Pat. No. 3,654,370 are prepared by the oxyalkylation of a polyhydric alcohol. The preferred starting materials are dihydric and trihydric alcohols such as propylene glycol or glycerol and propylene oxide or ethylene oxide. Copolymer polyols of ethylene oxide and propylene oxide are also useful.

The molecular weight of the polyol is determined by the number of moles of epoxide that are reacted with the alcohol initiator. Since the addition is random, the final alkoxylation product will not be a pure compound but, rather, will be a mixture of polyoxyalkylene polyols. For example, if the polyol is a polyol prepared by reacting glycerol or trimethylol propane with propylene oxide, using an amount of propylene oxide adequate to provide for an average molecular weight of about 1,000, the final propoxylation product will actually be composed of a mixture of polyoxypropylene triols having molecular weights varying from about 800 to about 1,200, the molecular weight distribution following a Gaussian distribution curve (sometimes referred to as a sine curve or a Poissan curve). As the molecular weight of the polyol increases, the spread in the molecular weights will also increase. Thus, when the average molecular weight of the triol is about 3,000, the deviation will be about ±400 molecular weight units so that most of the product will fall within the molecular weight range of about 2,600 to about 3,400.

As the molecular weight is still further increased, the percentage of free hydroxyl groups in the reaction mixture will decrease because of the added bulk of the already formed polyol, thus making the addition of more propylene oxide groups progressively more difficult. As a practical matter, when the triol reaches an average molecular weight of about 5,000, further propoxylation is accomplished only with extreme difficulty. The 5,000 molecular weight polyoxypropylene triols will have a molecular weight distribution of about ±1,000 so that the actual molecular weight range will be from about 4,000 to about 6,000. Again, the molecular weight distribution following a Gaussian distribution curve.

A further complication is encountered during the propoxylation to the higher molecular weights. As the reaction time and temperature are increased to encourage propoxylation, there is introduced a tendency on the part of the propylene oxide to isomerize to allyl alcohol and a tendency on the part of the hydroxypropyl end groups of the polyoxypropylene triol to dehydrate to form a terminal olefin group and water. Both the water and the allyl alcohol are susceptible to oxyalkylation thereby diluting the polyoxypropylene diol with undesired generally low molecular weight diol contaminants derived from the water and monofunctional allyl alcohol propoxylates. From as little as one percent to as much as ten percent of the oxypropyl end groups of the triol may dehydrate to form groups with terminal unsaturation in increasing the average molecular weight from about 3,000 to about 5,000.

When a polyoxypropylene polyol of this nature is reductively aminated in accordance with the procedure f Yeakey U.S. Pat. No. 3,654,370, comparatively higher temperatures and longer reaction times are required as the molecular weight of the polyol increases. This can result in the cleavage of the polyol to form undesired and unwanted alkyl ether by-products and hydrogenation of the unsaturated groups on the polyol to form propyl ethers.

Thus, although the results obtained heretofore with polyoxyalkylene diamines and triamines of the type disclosed by Yeakey have been generally satisfactory, problems such as those mentioned above have detracted from the utility of the products.

SUMMARY OF THE INVENTION

In accordance with the present invention, molecular weight distribution and terminal unsaturation problems such as those mentioned above are significantly reduced through the provision of aromatic amidoamine condensation products containing terminal primary amine groups which are analogous in function and reactivity to the polyoxyalkylene polyamines of Yeakey et. al.

Another significant property of the aromatic amidoamide condensation products of the present invention, as compared with the corresponding polyoxyalkylenepolyamines, is the desirable increase in "stiffners" or "hardners" that is obtained without otherwise adversely affecting the other properties of the amidoamines. For example, when the higher molecular weight polyoxyalkylene polyamines are used to cure epoxy resins, the resultant cured epoxy resin will frequently exhibit undesirable flex and impact properties and other related properties attributable to the "rubbery" nature of the high molecular weight polyoxyalkylene polyamines. Thus, it is frequently necessary to use additives and/or fillers to provide a final cured epoxy resin having the desired physical properties. The aromatic amidoamide condensation products of the present invention being significantly stiffer, can be used successfully with lesser quantities of fillers and/or additives or even without additives. The addition of these amide groups adds phase mixing advantages (when used as epoxy curing agents) over conventional polyoxyalkylene polyamines in many situations.

The improvements of the present invention are obtained by reacting the polyoxyalkylene polyamine component with the carboxylic acid component in an amount such that 1 mole of the polyoxyalkylene polyamine reacts with each carboxyl group of the aromatic polycarboxylic acid component.

Thus, it has been discovered in accordance with the present invention, that when the amine is in excess, as described, a primary amine group of the polyamine will preferentially condense with each of the carboxyl groups of the aromatic di- or tricarboxylic acid, ester or anhydride thereof and be linked thereto through an amide linkage. The condensation product is substantially free from terminal carboxylic acid groups and contains primarily terminal primary amine groups.

The condensation reaction between the polyoxyalkylene polyamine and the aromatic carboxylic acid, ester or anhydride thereof, is preferably conducted in an autoclave and at a temperature of from about 150° to about 250° C. The reaction time required for completion of the reaction will normally range from about 0.5 to about 12 hours. By-product water of reaction is preferably removed as formed, so that the reaction product obtained at the end of the reaction is the desired final product.

The reaction is preferably conducted at atmospheric pressure. Higher or lower pressures, such as pressures ranging from about 40 mm of mercury to about 3,000 psig may be used, if desired, but there is no particular advantage in so doing.

DETAILED DESCRIPTION

The block aromatic polyoxyalkylene polyamidopolyamine condensation products of the present invention will have a molecular weight of about 370 to about 12,000 and are prepared by reacting the polyoxyalkylene polyamine component with the carboxylic acid component in an amount such that 1 mole of the polyoxyalkylene polyamine reacts with each carboxyl group of the polycarboxylic acid component.

The block aromatic polyoxyalkylene polyamidopolyamine condensation products of the present invention will contain terminal primary amine groups derived from the polyoxyalkylene polyamine component and will be substantially completely free from terminal carboxyl groups.

THE DICARBOXYLIC ACID COMPONENT

The aromatic polycarboxylic acid component is selected from the group consisting of $C_8$ to $C_{20}$ benzene dicarboxylic acids, benzene tricarboxylic acids, naphthalene carboxylates, hemimellitic acid, 1,1,3-trimethyl-3-phenylindan-4',5-dicarboxylic acid, trimellitic acid, 2-phenyl pentanedioic acid and phenyl succinic acid, and anhydrides and $C_1$ to $C_4$ alkyl esters thereof.

Examples of aromatic dicarboxylic acid and tricarboxylic acids that may be used as starting materials for the present invention include acids such as terephthalic acid, isophthalic acid, trimesic acid, 1,1,3-trimethyl-3-phenylidan-4',5-dicarboxylic acid, 2,6-naphthalene dicarboxylic acid, t-butyl isophthalic acid, etc. (i.e., benzene dicarboxylic acids and tricarboxylic acids, hemimellitic acid, trimellitic acid, 2-phenyl pentanedioic acid, phenyl succinic acid, etc.).

THE POLYOXYALKYLENE POLYAMINE COMPONENT

The polyoxyalkylene polyamine component is selected from the group consisting of polyoxyethylene diamines, polyoxypropylene diamines, polyoxyethylene/oxypropylene diamines and polyoxypropylene triamines. In general, the average molecular weight of the polyoxyalkylene polyamine starting material will be from about 200 to about 6,000.

An advantage is obtained when using lower molecular weight diamine and triamine starting materials such as those having average molecular weights of about 200 to about 3,000 in that the final products will have primary amine functionalities and higher molecular weights but will contain significantly fewer contaminants than polyoxyalkylenepolyamines of a molecular weight of about 3,000 to 5,000 of the type formed by the reductive amination of oxypropylation adducts of dihydric and trihydric alcohols with propylene oxide.

Examples of polyoxypropylenediamines that may be used include those that are sold by the Texaco Chemical Company as Jeffamine ® D-series products having the formula:

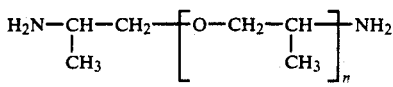

wherein n is a positive number having an average value of about 1 to about 50.

Representative products having this structural formula include polyoxypropylene diamines having an average molecular weight of about 230 wherein the value of n is about 2.6 Jeffamine ® D-230 amine), polyoxypropylene diamines having an average molecular weight of about 400 wherein n has a value of about 5.6 (Jeffamine ® D-400 amine), and a polyoxypropylene diamine product having an average molecular weight of about 2,000 wherein n has a value of about 33 (Jeffamine ® D-2000 amine) and a product having an average molecular weight of about 4,000 wherein n has a value of about 60 (Jeffamine ® D-4005 amine).

As another example, the polyoxyethylenediamines to be used in accordance with the present invention have the formula:

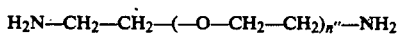

wherein n'' is a positive integer having a value of 1 to about 4. Representative compounds include bis-aminoethyl ether (where n'' is equal to 1), triethylene glycol diamine (where n'' is equal to 2) and tetraethylene glycol diamine (where n'' is equal to 3).

Another appropriate class of polyoxyalkylene diamines, containing both ethylene oxide and propylene oxide, which may be used are polyoxypropylene diamines that are sold by the Texaco Chemical Company as Jeffamine ® ED-series products having the formula:

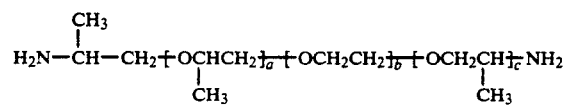

wherein a+c equals a positive number having a value of from about 2 to about 10 and b is a positive number having a value of from about 1 to about 50.

Examples of products having this general formula include a commercial product having an average molecular weight of about 600 where the value of b is about 13.5 and the value of a+c is about 3.5 (Jeffamine ® ED-600), a commercial product having an average molecular weight of about 900 wherein the value of a+c is again about 3.5, but the value of b is about 20.5 (Jeffamine ® ED-900). Other examples are those wherein a+c has a value of about 3.5 including a product having an average molecular weight of about 2,000 wherein the value of b is about 45.5 (Jeffamine ® ED-2001), and a product having an average molecular weight of about 4,000 wherein the value of b is about 85 (Jeffamine ® ED-4000) and also a product having an average molecular weight of about 6,000 wherein the value of b is about 132 and the value of a+c is about 4 (Jeffamine ® ED-6000).

Examples of appropriate polyoxypropylene triamines that may be used as a starting material for the present invention include triamines sold by Texaco Chemical Company as Jeffamine ® T-series products having the formula:

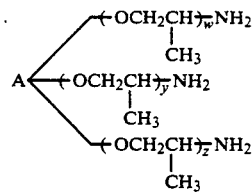

wherein A represents a trivalent hydrocarbon group consisting of 3 to 6 carbon atoms, resulting from the propoxylation of a propoxylation susceptible aliphatic trihydric alcohol containing 3 to 6 carbon atoms, and w, y and z are positive numbers and the average value of the sum of $w + y + z$ is from about 4 to about 100.

Examples of such products include a commercial product having an average molecular weight of about 400 sold by the Texaco Chemical Company under the tradename Jeffamine ® T-403 wherein A represents a trimethylol propane nucleus, and the product contains an average of about 5.3 oxypropylene groups, a product having an average molecular weight of about 3,000 sold by the Texaco Chemical Company under the tradename Jeffamine ® T-3000 wherein A represents a trimethylol propane nucleus and the product contains about 50 oxypropylene groups and a product having an average molecular weight of about 5,000 sold by the Texaco Chemical Company under the tradename Jeffamine ® T-5000 wherein A represents a glycerol nucleus and the product contains about 86 oxypropylene groups.

It is necessary to express "n" as an average number because, as pointed out above, the addition of ethylene oxide and/or propylene oxide proceeds randomly, and the addition will conform to a Gaussian distribution curve.

For example, if 1 mole of propylene glycol is reacted with 4 moles of ethylene oxide, under ethoxylation reaction conditions, the reaction, in theory, will proceed as follows:

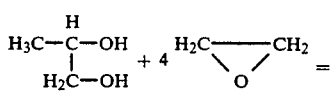

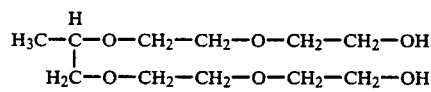

In this situation, the hydrocarbon group resulting from the propoxylation of propylene glycol will equal

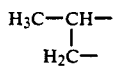

Since the addition of the ethylene oxide proceeds randomly, in conformance with a Gaussian distribution curve, in this example, some of the alkoxylation molecules will contain more than 4 moles of ethylene oxide and some will contain less than 4 moles of ethylene oxide.

As another example, Jeffamine R T-403 will have the formula:

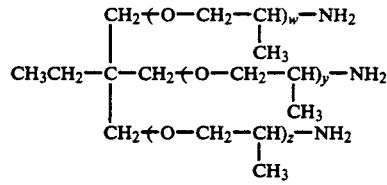

wherein, for Jeffamine ® T-403, the sum of $w + y + z$ will be about 5.3 and for Jeffamine ® T-3000, the sum of $w + y + z$ will be about 50. The addition of propylene oxide is random, and the molecules of the propoxylation product follow a Gaussian distribution pattern. A molecule wherein w and y equal 1 and z equals 98 will not be formed.

It is to be observed that in the above-written formula for Jeffamine ® T-403 and Jeffamine ® T-3000, the 6 carbon atom trivalent hydrocarbon group resulting from the propoxylation of trimethylolpropane will be:

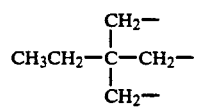

A variety of molecular configurations are possible for the amidoamine condensation products of the present invention, depending on the starting materials.

Thus, an aromatic carboxylic acid such as a tricarboxylic acid may be reacted with a polyoxyethylene diamine to provide a condensation product containing three primary amine groups, as illustrated by the following formula:

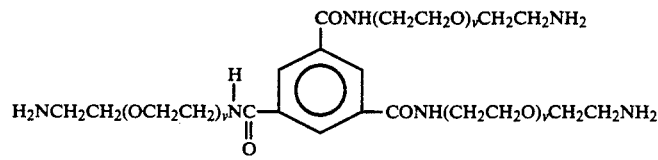

wherein v is a positive integer having a value of 1 to 4.

If an alkyl substituted aromatic dicarboxylic acid is used as the aromatic carboxylic acid component an a polyoxypropylene diamine is used as the polyoxyalkylene polyamine component, an aromatic amidoamine condensation product will be formed containing 2 primary amine groups, as illustrated by the following formula:

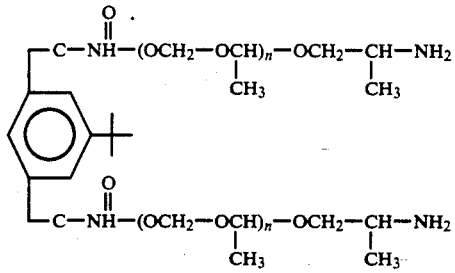

wherein n is a positive number having a value of 1 to about 50.

As yet another example, if the starting material that is used is a more complex dicarboxylic acid such as 1,1,3-trimethyl-3-phenylindan-4',5-dicarboxylic acid, the condensation product will have the formula:

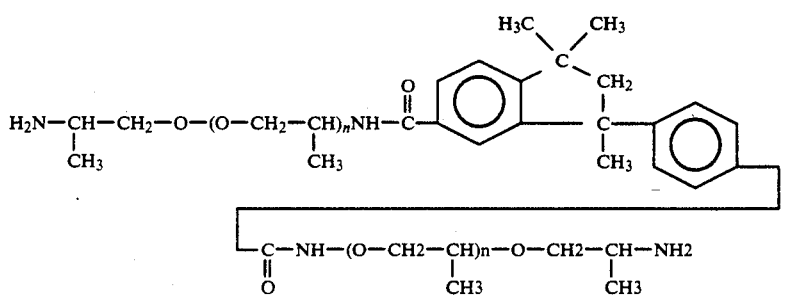

wherein n is a positive number having a value of 1 to about 50.

PREPARATION OF THE AMIDOAMINE CONDENSATION PRODUCT

It has been discovered in accordance with the present invention that an amidoamine condensation product is preferentially formed when an aromatic dicarboxylic or tricarboxylic acid or ester or anhydride thereof is reacted with an excess of a polyoxyalkylene diamine or triamine at autogenous pressure at a temperature within the range of about 150° to about 250° C. for a reaction time within the range of about 0.5 to about 12 hours. Normally, the reaction will go to completion after a reaction time within the range of about 2 to about 6 hours.

By-product water of reaction is preferably removed from the reaction mixture as formed. The reaction is complete when essentially all of the carboxylate groups have reacted with primary amine groups of the polyoxyalkylene diamine or triamine. Under the noncatalytic reaction conditions employed herein, the primary amine groups of the polyoxyalkylene diamine or triamine are essentially unreactive with each other.

A slight excess of the polyoxyalkylene polyamine component is preferably used, such as an excess of about 0.05 to about 0.2 mole, so that about 1.05 to about 1.2 moles of the polyoxyalkylene polyamine component are added for each catalyst group of the carboxylate feed component.

SPECIFIC EXAMPLES

Group I - Amidoamine Addition Products of a Dibasic Acid with a Polyoxyethylene Diamine A series of compounds were synthesized using terephthalic and isophthalic acids. Their properties are recorded in the attached table. Some highlights are cited below:

1. Most of these compounds are water and methanol soluble.
2. Most of these compounds are solid with varying melting points up to 150° C. However, some amines from isophthalic acid are liquid.
3. The product from terephthalic acid and BAEE (Bisaminoethyl ether) cannot be prepared under 200° C., since this salt melts at >200° C.
4. IR, amine and acidity analyzed support the structure of amidoamines.

EXAMPLE 1 (6103-99)

To a 100-ml 3-necked flask equipped with thermometer, stirrer, Dean-Stark trap and N2-flow line, was charged 24.9 g of terephthalic acid (0.15 mole) and Jeffamine ® EDR-148 amine (44.4g, 0.30 mole), heated to 200° C. and kept at this temperature for about 3 hours. During the process, 5.0 cc of water was removed (theoretically 5.4g). After cooling to room temperature, a white solid (mp 95°-102° C.) was recovered (60.2g). The amine analysis of this product indicated 4.34 meq/g (theoretical 4.55 meq/g). This material is soluble in water or methanol. IR showed the presence of amide. The results of other examples are summarized in the attached table.

TABLE I

| BIS-(AMIDOAMINE) SYNTHESIS - REACTIONS OF POLYOXYETHYLENE DIAMINES WITH DIBASIC ACID AT 2:1 MOLAR RATIO | | | |
|---|---|---|---|
| | BAEE | EDR-148[1] | EDR-192[2] |
| Terephthalic Acid | 6152-19 Solid salt at 200° C. Product cannot be made | 6103-99 mp ca. 140° C. Pale-yellow solid Soluble in $H_2O$, and MeOH IR: Amide | 6152-11 mp 75-82° C. Tan-colored, opaque solid Amine 3.40 meq/g (Theor. 3.9) Soluble in $H_2O$ and MeOH |
| Isophthalic Acid | 6152-20 mp ca. 80° C. Hard orange solid Soluble in $H_2O$ and MeOH | 6152-24 Brown liquid Amine 4.80 meq/g (Theor. 4.7) Acidity 0.29 meq/g Soluble in $H_2O$ and MeOH IR: Amide | 6152-23 Yellow liquid Amine 3.85 meq/g (Theor. 3.87) Acidity 0.18 meq/g Soluble in $H_2O$ and MeOH IR: Amide |

[1] Jeffamine$^R$ EDR-148 is an amine terminated triethylene glycol having the formula: $H_2N-CH_2CH_2-O-CH_2CH_2-O-CH_2CH_2-NH_2$.
[2] Jeffamine$^R$ EDR-192 is an amine terminated tetraethylene glycol having the formula: $H_2N-CH_2CH_2-O-CH_2CH_2-O-CH_2CH_2-O-CH_2CH_2-NH_2$ Jeffamine ® EDR-148 and Jeffamine ® EDR-192 are members of a group of compounds having the general formula:

$$H_2N-CH_2-CH_2-(O-CH_2-CH_2)_{n''}-NH_2$$

wherein $n''$ is a positive integer having a value of 1 to about 4.

High Molecular Weight Tetraamines from Polyoxypropylene Triamines and Dibasic Acids A process for preparing a series of tetraamines via coupling reaction of Jeffamine T-403 or T-5000 (polyoxypropylene triamines manufactured and sold by the Texaco Chemical Company) with various aromatic dibasic acids at a molar ratio of 2:1 is disclosed. The possible problem of gel formation during the reaction was not observed.

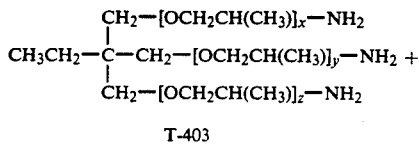

T-403

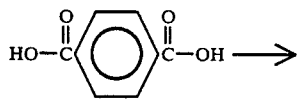

Terephthalic Acid

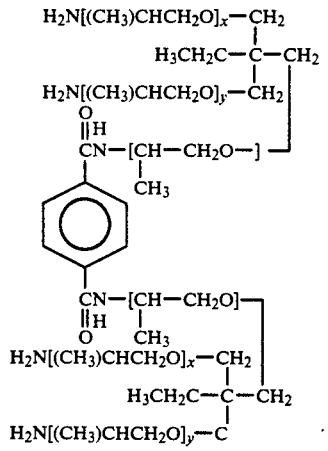

EXAMPLE 2 (6152-14)

The Reaction of Jeffamine ® T-403 amine and Terephthalic Acid (2:1 Molar Ratio)

To a 500-ml 3-necked flask equipped with a thermometer, mechanical stirrer, Dean-Stark trap and N$_2$-line was charged Jeffamine T-403 (202g ca. 0.5 mole) and terephthalic acid (41.5 g, ca. 0.25 mole). The reaction mixture was heated to 200° C. with stirring and nitrogen flow, for four hour period of time. During this process, 9.0g (0.5 mole) of water was generated and removed through the Dean-Stark trap. After cooling to room temperature, a pale-yellow, viscous product (227.8g) was recovered. The product was insoluble in water, but soluble in methanol and acetone. The total amine assay showed 3.57 meq/g (theoretical 3.7 meq/g based on Jeffamine T-403 at 6.45 meq/g). The acidity titration showed 0.03 meq/g, indicated the high conversion of adipic acid. The IR showed the amide absorption and polyether functionality.

Identical experimental procedures, as described in Example 2 were used, and the results are summarized in the following table:

TABLE II

PROPERTIES OF PRODUCTS FROM JEFFAMINE T-SERIES AMINES WITH VARIOUS DIBASIC ACIDS AT 2:1 MOLAR RATIO

|  | T-403 | T-5000 |
|---|---|---|
| Terephthalic Acid | 6152-14<br>Yellow, viscous transparent liquid<br>Amine 3.71 meq/g<br>Acidity < 0.003 meq/g<br>IR: Amide | 6103-83<br>Nearly colorless opaque liquid<br>Amine 0.43 meq/g<br>Acidity 0.12 meq/g<br>IR: Amide |
| Isophthalic Acid | 6152-15<br>White, slightly viscous, transparent liquid<br>Amine 3.66 meq/g<br>Acidity 0.32 meq/g<br>IR: Amide | 6152-18<br>Light yellow, transparent liquid<br>Amine 0.39 meq/g<br>Acidity 0.07 meq/g<br>IR: Amide |

Uses of the products of Example 2 include their application in the preparation of polyureas (by reaction with polyisocyanates), epoxy curing agents and crosslinking agents.

Amidoamines from t-Butyl Isophthalic Acid and Polyoxypropylene Daimines and Triamines Using an Amoco product - t-butyl isophthalic acid and JEFFAMINE ® amines manufactured by the Texaco Chemical Company, including JEFFAMINE ® EDR-148, EDR-192, D-230, D-2000, ED-2001, T-403, T-3000 and T-5000, a series of amidoamines have been prepared.

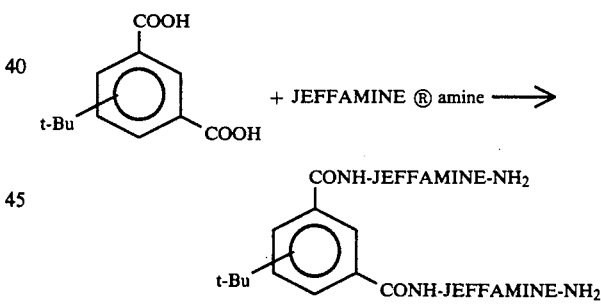

These amines can be active amines, (from EDR-amine series), tetrafunctional amine (from T-series amines), water-soluble amine (from ED-2001), etc. The applications include epoxy curing material, polyamide or polyurea uses.

The alkyl and phenyl groups in the structure can be an important factor contributing to the specific applications, such as increasing compatibility with the monomer component.

EXAMPLE 3 t-Butyl Isophthalic Acid+EDR-148 (1:2)

To a 500 ml 3-necked flask equipped with a thermometer, Dean-Stark trap, stirrer and N2-line was charged t-butyl isophthalic acid (Amoco t-butyl IPA, 111 g, 0.5M) and EDR-148 (Texaco product, 148g, 1.0M). The mixture was heated to 185°-215° C. for four hours to remove water (ca. 22 cc). After cooling to room temperature, a yellow solid was obtained (226.5g). The analysis indicated.- total amine 3.81 meq/g (theoretical 4.1 meq/g) and acidity 0.06 meq/g.

Other examples involving EDR-192, D-230, D-2000, ED-2001, T-403, T-3000 and T-5000 are summarized in the attached table.

TABLE III
AMIDOAMINES FROM T-BUTYL ISOPHTHALIC ACID AND JEFFAMINE ® AMINES

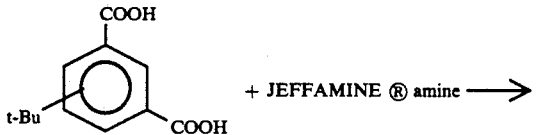

| Notebook No. | JEFFAMINE ® Amine* | Properties of Product |
|---|---|---|
| 6199-57 | EDR-148 | Semisolid yellow<br>Amine 3.81 meq/g (4.1)<br>Acidity 0.06 meq/g |
| 6199-60 | EDR-192 | Solid viscous, transparent, light yellow<br>Amine 3.32 meq/g (3.3)<br>Acidity 0.06 meq/g |
| 6199-61 | D-230 | Solid white transparent<br>Amine 2.41 meq/g (2.9)<br>Acidity 0.15 meq/g |
| 6199-68 | D-2000 | Liquid brown, transparent<br>Amine 0.43 meq/g (0.47)<br>Acidity 0.11 meq/g |
| 6199-72 | ED-2001 | Solid light brown, mp 42, water soluble<br>Amine 0.59 meq/g<br>Acidity 0.10 meq/g |
| 6199-69 | T-403 | Liquid viscous, light yellow, transparent<br>Amine 3.56 meq/g (3.57)<br>Acidity 0.08 meq/g |
| 6199-70 | T-3000 | Liquid light yellow, transparent<br>Amine 0.57 meq/g<br>Acidity 0.08 meq/g |
| 6199-73 | T-5000 | Liquid yellow, transparent<br>Amine 0.33 meq/g (0.39) |

Acidity 0.69 meq/g

*Molar ratio of t-BuIPA:Amine = 1:2

EXAMPLE 3-A

Usage of Product T-BuIPA+T-403 (from 6199-69)

The mixture of 6199-69 product 21.0g and Epon 828 (from Shell 28g) was mixed thoroughly and poured into a mold and cured at 80° C. overnight. A yellowish white rigid material was made.

Amidoamines from Trimesic Acid and Polyoxyethylene or Polyoxypropylene Diamines or Triamines Using trimesic acid as the coupling agent, a series of new amidoamines can be prepared. The synthesis is described as follows:

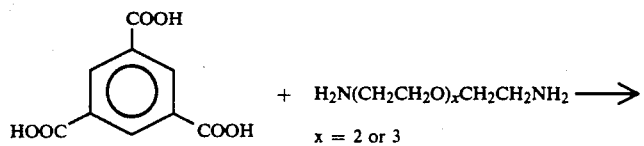

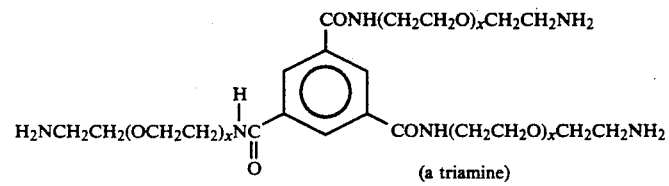

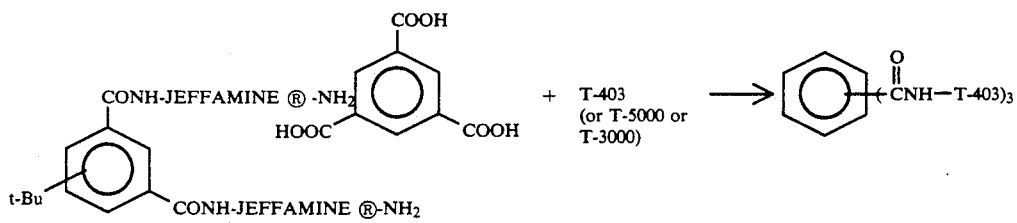

Light colored liquids were obtained from T-series amines and D-2000. Light colored transparent solids were obtained from EDR-series amines. A crystalline yellowish solid was obtained from ED-6000.

EXAMPLE 4 (6152-25)

To a 250 ml 3-necked flask equipped with a thermometer, Dean-Stark trap, stirrer and N2-line was charged with JEFFAMINE® T-403 (182g, 0.396 mole) and trimesic acid (44.4g, 0.21 mole). The mixture was heated to 200° C. for four hours. During the process, ca. 6.0 cc water was collected in the Dean-Stark trap. After cooling to room temperature, a transparent, light-yellow liquid was recovered (204g) that was non-pourable at room temperature. The analysis showed 3.65 meq/g amine, 0.26 meq/g acid. The IR showed the formation of amide.

Results of other examples, including T-403 at various ratios, T-5000, T-3000, D-2000, D-4000, ED-6000 are in the attached table. The comparative example using citric acid showed the difference between two tribasic acids. The result of trimesic acid to T-403 at 1:1 molar ratio, giving unworkable cross-linkage polyamide indicated the importance of feedstock ratio.

Example 4-A (6152-36)

In a similar manner, three moles of Jeffamine® T-403 amine was allowed to react with one mole of trimesic acid. The resulting product was almost colorless and showed 4.05 meq/g of amine (theory 3.8) and 0.17 meq/g of acid. This product (11.4g) was mixed with 18.5g of Epon 828 (Shell). The reactants began to react very slowly and after two hours the mixture was very thick, but still stirable. The mixture was used to seal two steel coupons together. The reactants cured to an extremely hard resin.

TABLE IV
PROPERTIES OF PRODUCTS FROM TRIMESIC ACID AND JEFFAMINE AMINES

| Notebook No. | Amine | Mole Ratio of Acid to Amine | Properties | Analysis $-NH_2$ meq/g | $-COOH$ meq/g | IR Amide |
|---|---|---|---|---|---|---|
| 6152-25 | T-403 | 1:2 | Transparent, light yellow, viscous liquid-or-solid | 3.65 | 0.26 | Yes |
| 6152-37 | T-403 | 1:1 | Hard solid at 200° C. | — | — | |
| 6152-36 | T-403 | 1:3 | Transparent, light yellow, Fluidable liquid, Sol. in MeOH, Insol. in $H_2O$ | 4.05 | 0.17 | Yes |
| 6152-35 | T-3000 | 1:3 | Nearly colorless clear liquid | 0.60 | 0.06 | Yes |
| 6152-32 | T-5000 | 1:3 | Transparent, light yellow liquid, sol. in MeOH | 0.40 | — | Yes |
| 6152-26 | EDR-192 | 1:3 | Soft, sticky solid (golden yellow) sol. in MeOH, insol. in acetone, $H_2O$ | 3.20 | 0.14 | Yes |
| 6152-39 | EDR-148 | 1:3 | Soft, sticky solid (golden yellow) sol. in MeOH, insol. in acetone, $H_2O$ | 4.90 | 0.11 | |
| 6152-40 | D-4000 | 1:3 | Transparent, light yellow liquid | 0.24 | 0.06 | |
| 6152-42 | ED-6000 | 1:3 | Opaque, light grey crystalline solid | 0.18 | 0.10 | |
| 6152-43 | (with citric acid) | 1:3 liquid | Black, viscous | — | — | |
| 6152-53 | D-2000 | 1:3 | Light yellow liquid, sol. in MeOH, insol. in $H_2O$ | 0.54 | 0.12 | Yes |

(where JEFFAMINE® amine = EDR-192, D-2000, D-4000, ED-6000, ED-2001, T-403 or T-5000).

These amines, containing a naphthalene-functionality can be a diamine (from JEFFAMINE® diamine), a tetra-amine (from JEFFAMINE triamine) or a water soluble amine (from JEFFAMINE ED-series amine). In comparative examples, in contrast to dimethyl 2,6-naphthalene dicarboxylate another precursor, 2,6-naphthalene dicarboxylic acid afforded decomposing products. These results are summarized in a table. One of the uses of these products as an epoxy resin was demonstrated.

Di- and Tetraamidoamines from 2,5-Naphthalene Dicarboxylate and Polyoxyethylene and Polyoxypropylene Diamines and Triamines A series of novel di- and tetra-amines have been prepared from the reaction of JEFFAMINE® amines and dimethyl 2,6-naphthalene dicarboxylates according to the following reaction:

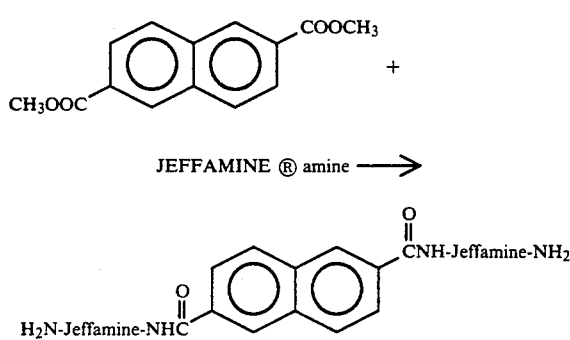

EXAMPLE 5:
Reaction of DM-2,6-NDC and JEFFAMINE® T-403 (1 2 Molar Ratio) (6153-4

To a 250-ml 3-necked flask equipped with thermometer, mechanical stirrer, Dean-Stark trap and $N_2$-inlet-outlet line, charge dimethyl 2,6-naphthalene dicarboxylate (Amoco product 36.6g, 0.15M) and JEFFAMINE® T-403 (138g, 0.3 mole). The mixture was heated to 200° C., under nitrogen atmosphere and held for 2.5 hours. After cooling to room temperature, a highly viscous, light colored liquid was obtained (157g). The analysis indicated amine content 3.79 meq/g, acidity 0.29 meq/g. IR spectrum showed the formation of amide.

EXAMPLE 5-A:
Usage of DM-2,6-NDC-T-403 Adduct (6153-4A)

A mixture of product (from 6153-4) (39.6g, ca. 0.15 meq) and Epon 828 (Shell product) (56.1g, 0.30 meq/g) was stirred thoroughly and then poured to a mold. The mixture was cured at ca. 70° C. A rigid epoxy resin material was made.

Other examples are cited in Table V.

EXAMPLE 5-B:

Comparative Example Using 2,6-Naphthalene Dicarboxylic Acid (6152-73)

Following Example 5 procedures, a mixture of 2,6-naphthalene dicarboxylic acid (10.8g) and JEFFAMINE D-2000 (200g) was heated to 200-220° C. for a few hours. The final product obtained was dark black liquid with analysis of 0.84 meq/g amine and 0.42 meq/g acidity. The use of 2,6-naphthalene dicarboxylic acid gave a decomposed product. These negative results indicated the importance of using a suitable precursor - diester of 2,6-naphthalene dicarboxylic acid.

TABLE V

DI- AND TETRA-AMINES FROM DIMETHYL-2,6-NAPHTHALENE DICARBOXYLATE AND JEFFAMINE ® AMINES

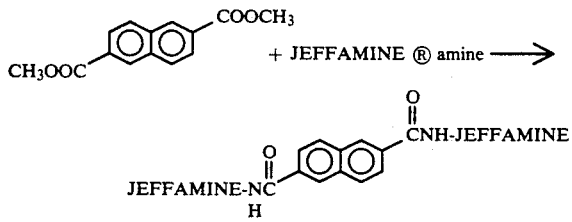

| Notebook No. | JEFF-AMINE ® Amine | Products Analysis* —NH2 | —COOH | Properties |
|---|---|---|---|---|
| 6152-99 | EDR-192 | 3.14 / 3.3 | 0.26 | Solid white mp ca. 75° C. IR:Amide |
| 6153-2 | EDR-148 | — | — | mp >200° C. |
| 6153-35 | D-2000 | 0.66 (0.47) | 0.16 | Liquid brown IR:Amide |
| 6153-14 | D-400 | 1.98 (1.90) | 0.41 | Solid waxy yellow IR:Amide |
| 6153-13 | ED-600 | 1.60 (1.3) | 0.43 | Liquid transparent yellow Water soluble |
| 6153-97 | ED-2001 | 0.65 (0.48) | 0.14 | Solid crystalline Water soluble |
| 6153-4 | T-403 | 3.79 (3.50) | 0.29 | Liquid yellow, viscous |
| 6153-81 | T-5000 | 0.44 (0.4) | 0.06 | Liquid yellow |

*Analysis: Amine and acidity in meq/g. Calculated figures in parenthesis.

Amidoamines from Nonconjugated Aromatic Dicarboxylic Acids and Polyoxypropylene Diamines and Triamines and Polyoxyethylene Diamines AMOCO ® PIDA (1,1,3-trimethyl-3-phenylindan-4',5-dicar- boxylic acid) is a "non-conjugated", non-planar diacid, containing both alkyl- and aromatic functionalities. The uses of this diacid enable us to prepare a series of novel amines, from the reactions of PIDA and JEFFAMINE ® amines including JEFFAMINE T-403, T-3000, T-5000, D-2000, D-4000, ED-600, EDR-192, EDR-148 and BAEE (bis-aminoethyl ether).

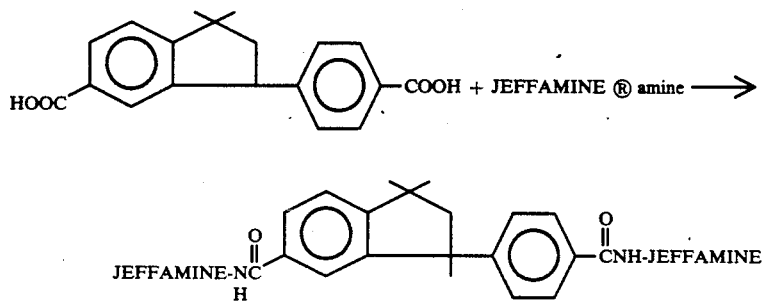

These products are light colored semisolid liquids and soluble in alcohol solvents, except (1) the product from ED-600 was soluble in water with the phenomenon of inverse solubility factor at 29-41° C. and (2) the product from BAEE could not be prepared under the reaction conditions we used, due to the high melting point of this amine-acid salt.

The product will be useful in a number of applications, such as polyurea and epoxy resin. A specific usage in the area of epoxy resin has been exemplified.

EXAMPLE 6

(6152-48)

To a 250-ml 3-necked flask equipped with thermometer, stirrer, Dean-Stark trap and N2 inlet-outlet line was charged AMOCO ® PIDA (12.1g, 0.037 mole) and JEFFAMINE ® D-2000 amine (150g, 0.075 mole). The mixture was heated to 210° C. for 2 hours, then cooled to room temperature. A transparent, light brown liquid product was recovered (228g). The analysis showed 0.52 meq/g amine (calc. 0.47 meq/g), acidity 0.15 meq/g and water content 0.06%. The IR showed the formation of amide.

EXAMPLE 6-A (6152-49)

To a 250-ml 3-necked flask equipped with thermometer, stirrer, Dean-Stark trap and N2 inlet-outlet line was charged AMOCO ® PIDA (64.9g, 0.20 mole) and JEFFAMINE ® EDR-192 amine (76.8g, 0.40 mole). The mixture was heated to 200° C. for four hours. During the process, ca. 7.0 cc of water was removed through the Dean-Stark trap. After cooling to room temperature, a yellowish semisolid product was recovered (61.5g). This product was soluble in methanol and insoluble in water. The analyses indicated amine, 3.0 meq/g (calc. 3.0 meq/g), acidity 0.08 meq/g. The IR analysis indicated the formation of amide.

Other examples are cited in Table VI.

EXAMPLE 6-B (6152-48B)

A soap dish was made by mixing 77g of 6152-48 (reaction product from AMOCO® PIDA and JEFFAMINE® D-2000) and 15g of Epon 828 (diglycidol ether of bisphenol-A from Shell) and pouring the contents in an elastic mold. The material was cured overnight in an oven set at 80° C. The material was soft and rubbery solid.

EXAMPLE 6-C (6152-48B)

Repeated the previous example using the mixture of 48g of 6152-48, 6.6g of dipropyl-triamine (DPTA) and Epon 828 56.1g. After curing at 80° C. for overnight, a hard solid with some flexibility was made.

TABLE VI

PROPERTIES OF PRODUCTS FROM AMOCO PIDA AND JEFFAMINE$^R$ AMINES

| Notebook No. | Amine | Molar Ratio of Acid to Amine | Analyses $-NH_2$ meq/g | Analyses $-COOH$ meq/g | Notes |
|---|---|---|---|---|---|
| 6152-68 | T-403 | 1:2 | 3.4 | 0.21 | Yellow, semisolid |
| 6152-66 | T-3000 | 1:2 | 0.63 | 0.08 | Light color liq. |
| 6152-89 | T-5000 | 1:2 | 0.38 | 0.11 | Yellow liquid |
| 6152-71 | T-5000 | 1:3 | 0.40 | 0.08 | Yellow liquid |
| 6152-48 | D-2000 | 1:2 | 0.52 | 0.15 | Transparent, light-brown liq. |
| 6152-65 | D-4000 | 1:2 | 0.26 | 0.10 | Brown liquid |
| 6152-69 | ED-600 | 1:2 | 1.26 | 0.13 | Light yellow liq. soluble in H$_2$O ISF at 29-41° C. |
| 6152-49 | EDR-192 | 1:2 | 3.0 | 0.08 | Yellow, semisolid |
| 6152-50 | EDR-148 | 1:2 | 4.2 | 0.25 | Yellow solid |
| 6152-51 | BAEE | 1:2 | — | — | High m.p. salt |

*Products are soluble in MeOH and insoluble in H$_2$O, except ED-600 product.

The foregoing examples have been given by way of illustration only and are not intended as limitations on the scope of this invention, which is defined by the appended claims.

We claim:

1. A method of preparing a block polyamido polyamine condensation product, said block polyamido polyamine condensation product being the condensation product of isophthalic acid with bis-aminoethyl ether, said method comprising the steps of:
   (a) reacting said isophthalic acid,
   (b) with about 1.05 to about 1.2 moles of said bisaminoethyl ether per mol of isophthalic acid,
   (c) said isophthalic acid being reacted with said bis-aminoethyl ether in an amount sufficient to react each carboxyl group of said isophthalic acid with 1 mol of said bis-aminoethyl ether under reaction conditions including a temperature within the range of about 150° to about 250° C., a pressure of about 40 mm to about 3,000 psig and a reaction time of about 0.5 to about 12 hours, sufficient to form said block amidoamine reaction product, said amidoamine reaction product having terminal groups consisting essentially of primary amine groups,
   (d) the amidoamine being a water soluble, methanol soluble solid having a melting point of about 80° C.

* * * * *